United States Patent
Kang et al.

(10) Patent No.: US 10,551,326 B2
(45) Date of Patent: Feb. 4, 2020

(54) METHOD FOR MEASURING SEMICONDUCTOR DEVICE

(71) Applicant: SAMSUNG ELECTRONICS CO., LTD., Suwon-si, Gyeonggi-do (KR)

(72) Inventors: Hyo Hyeong Kang, Hwaseong-si (KR); Kang Woong Ko, Seoul (KR); Sung Yoon Ryu, Suwon-si (KR); Gil Woo Song, Hwaseong-si (KR); Jae Hyung Ahn, Suwon-si (KR); Chul Hyung Yoo, Suwon-si (KR); Kyoung Hwan Lee, Hwaseong-si (KR); Sung Ho Jang, Suwon-si (KR); Yong Ju Jeon, Seongnam-si (KR); Hyoung Jo Jeon, Suwon-si (KR)

(73) Assignee: SAMSUNG ELECTRONICS CO., LTD., Suwon-si, Gyeonggi-do (KR)

(*) Notice: Subject to any disclaimer, the term of this patent is extended or adjusted under 35 U.S.C. 154(b) by 0 days.

(21) Appl. No.: 15/855,520

(22) Filed: Dec. 27, 2017

(65) Prior Publication Data
US 2018/0202942 A1 Jul. 19, 2018

(30) Foreign Application Priority Data
Dec. 28, 2016 (KR) .................. 10-2016-0180918

(51) Int. Cl.
*G01N 21/95* (2006.01)
*H01L 21/66* (2006.01)
*G06K 9/03* (2006.01)
*G06K 9/62* (2006.01)
(Continued)

(52) U.S. Cl.
CPC ......... *G01N 21/9501* (2013.01); *H01L 22/20* (2013.01); *H01L 21/67288* (2013.01)

(58) Field of Classification Search
CPC ... G06K 9/00557; G06T 7/001; G06T 7/0004; G01N 21/4788; G01N 21/9501; G01N 21/956
See application file for complete search history.

(56) References Cited

U.S. PATENT DOCUMENTS

| 5,739,909 A | 4/1998 | Blayo et al. |
| 6,476,912 B1 | 11/2002 | Nakazawa |
| 6,897,955 B2 | 5/2005 | Wielsch et al. |

(Continued)

FOREIGN PATENT DOCUMENTS

| KR | 10-0389566 B1 | 6/2003 |
| KR | 10-0450505 B1 | 9/2004 |

*Primary Examiner* — Brian Turner
(74) *Attorney, Agent, or Firm* — Lee & Morse, P.C.

(57) ABSTRACT

A method for measuring a semiconductor device is provided. A method for measuring a semiconductor device includes defining an interest area and an acceptable area in a chip area on a wafer; performing a first measurement of the chip area with a spectral imaging device to acquire spectrum data of the chip area; assuming the distribution of the spectrum data of a first pixel in the acceptable area is a normal distribution; calculating a distance from a central point on the normal distribution to second pixels in the interest area; selecting a position of a second pixel having a distance from the central point on the normal distribution greater than a predetermined range, among the second pixels, as a candidate position; and performing a second measurement of the candidate position.

16 Claims, 8 Drawing Sheets

(51) Int. Cl.
*G01N 21/88* (2006.01)
*H01L 21/67* (2006.01)

(56) References Cited

U.S. PATENT DOCUMENTS

| | | |
|---|---|---|
| 6,909,507 B2 | 6/2005 | Norton et al. |
| 7,092,096 B2 | 8/2006 | Tao et al. |
| 7,242,015 B2 | 7/2007 | Shinada et al. |
| 7,289,219 B2 | 10/2007 | Norton et al. |
| 7,477,960 B2 | 1/2009 | Willis et al. |
| 7,508,510 B2 | 3/2009 | Pfeiffer et al. |
| 7,522,295 B2 | 4/2009 | Vuong et al. |
| 7,532,328 B2 | 5/2009 | Nara et al. |
| 8,064,038 B2 | 11/2011 | Brouwer et al. |
| 9,146,479 B2 | 9/2015 | Hasegawa et al. |
| 2007/0177787 A1* | 8/2007 | Maeda ............... G06K 9/00557 382/141 |
| 2009/0231355 A1* | 9/2009 | Perronnin ............... G09G 5/06 345/594 |
| 2012/0141012 A1* | 6/2012 | Sakai ............... G01N 21/9501 382/149 |
| 2014/0002632 A1 | 1/2014 | Lin |
| 2014/0204203 A1 | 7/2014 | Lihardt et al. |
| 2014/0358485 A1 | 12/2014 | Lee et al. |
| 2016/0153915 A1 | 6/2016 | Ko et al. |
| 2017/0147909 A1* | 5/2017 | Izumi ................... G06K 9/6262 |

\* cited by examiner

METHOD FOR MEASURING SEMICONDUCTOR DEVICE

CROSS-REFERENCE TO RELATED APPLICATION

Korean Patent Application No. 10-2016-0180918, filed on Dec. 28, 2016, in the Korean Intellectual Property Office, and entitled: "Method for Measuring Semiconductor Device," is incorporated by reference herein in its entirety.

BACKGROUND

1. Field

The present disclosure relates to a method for measuring a semiconductor device.

2. Description of the Related Art

In order to distinguish between acceptable/defective semiconductor devices, for example, whether structures of semiconductor patterns formed on a chip die on a wafer, e.g., the thicknesses of the semiconductor patterns, are included within a design range or exceed the design range, various types of measurements may be performed. For example non-contact and non-destructive measurement apparatuses that measure the thickness using X-ray, sound wave, or light, may be used that do not process or deform a sample to be measured, e.g., a semiconductor substrate.

Among the non-destructive measurement apparatuses, a spectral imaging device measures the entire wafer and outputs the spectrum results thereof. When using the spectral imaging device, although it is possible to quickly measure the spectrum over the entire areas of the wafer, it takes more time to perform the spectrum analysis than a sampling point measurement type.

SUMMARY

According to an embodiment of the present disclosure, there is provided a method for measuring a semiconductor device including defining an interest area and a acceptable area in a chip area on a wafer; performing a first measurement of the chip area with a spectral imaging device to acquire spectrum data of the chip area; assuming the distribution of the spectrum data of the first pixel in the acceptable area is a normal distribution; calculating a distance from a central point on the normal distribution for second pixels in the interest area; selecting a position of a second pixel having a distance from the central point on the normal distribution greater than a predetermined range as a candidate position; and performing a second measurement of the candidate position.

According to another embodiment of the present disclosure, there is provided a method for measuring a semiconductor device including defining an interest area and an acceptable area in a chip area on a wafer; performing a first measurement of the chip area with a spectral imaging device to acquire spectrum data of the chip area; calculating a Mahalanobis distance on second pixels in the interest area from the distribution of spectrum data of the first pixel in the acceptable area; generating a Mahalanobis distance map in which the Mahalanobis distance of the second pixel is expressed by a numerical value of intensity; selecting the position of a second pixel having an intensity greater than a predetermined value, among the second pixels, as a candidate position; and performing a second measurement of the candidate position.

According to still another embodiment of the present disclosure, there is provided a method for measuring a semiconductor device including defining an interest area and an acceptable area in a chip area on a wafer; performing a first measurement of the chip area with a spectral imaging device to acquire spectrum data of the chip area; selecting a candidate position of a second pixel in the interest area, based on spectrum data of a first pixel in the acceptable area; performing a second measurement on the candidate position; and predicting a measurement of the pixel other than the interest area, using the second measurement of the candidate position.

According to still another embodiment of the present disclosure, there is provided method for manufacturing a semiconductor device, the method including forming the semiconductor device in a chip area on a wafer that includes at least one other chip area, and measuring the semiconductor device, wherein measuring the semiconductor device includes performing a spectral analysis of the chip area, selecting a candidate position in accordance with the spectral analysis, and performing point sampling analysis on the candidate position.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
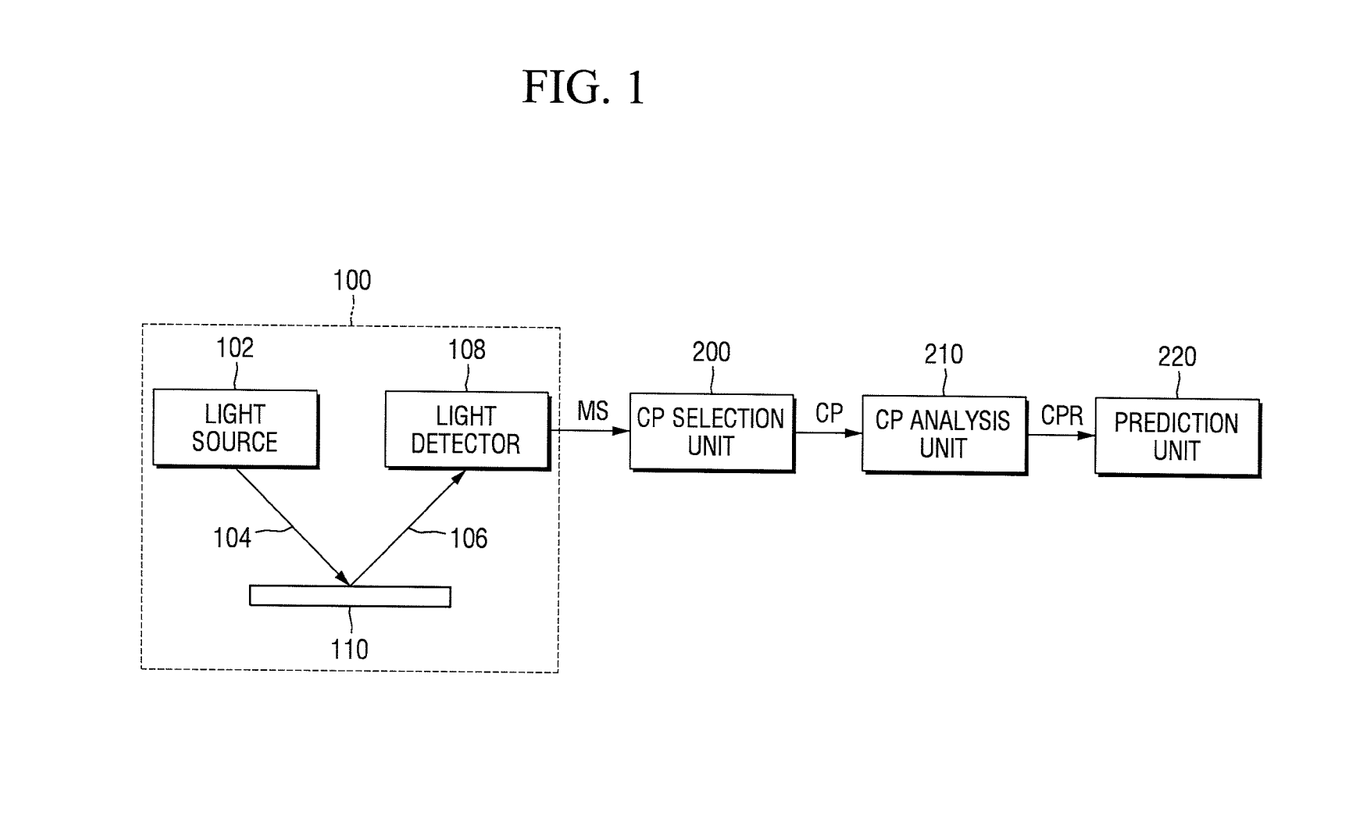
FIG. 1 illustrates a schematic diagram of a device for measuring a semiconductor device according to an embodiment of the present disclosure.
Figure 2:
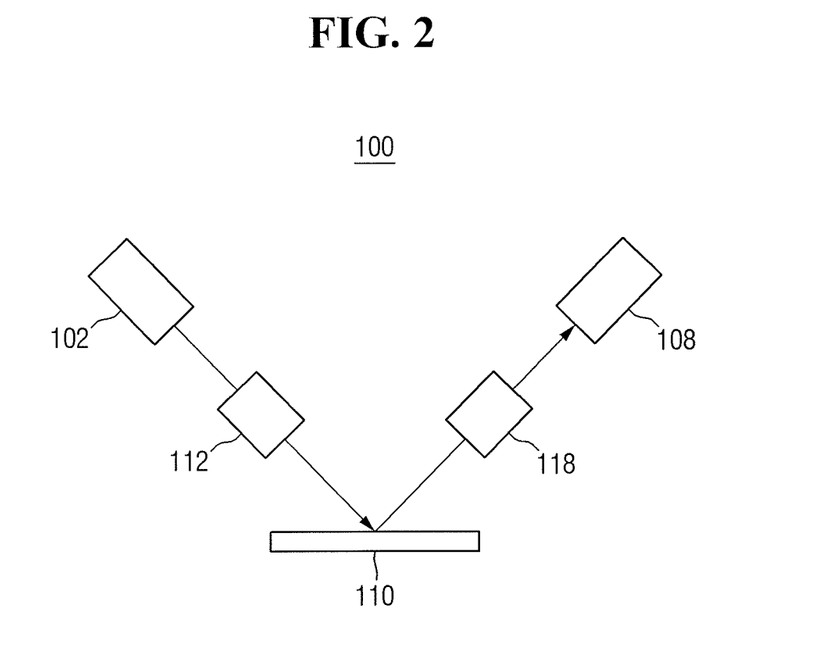
FIG. 2 illustrates a diagram of the optical measurement apparatus of FIG. 1 in detail.

FIG. 1 is a schematic diagram of a device for measuring a semiconductor device according to an embodiment of the present disclosure. FIG. 2 is a diagram illustrating the optical measurement apparatus of FIG. 1 in detail.

Referring to FIG. 1, an object to be measured 110 according to an embodiment of the present disclosure may be a wafer. Specifically, the object to be measured 110 may be a chip area (chip die) on the wafer.

The chip area may include various semiconductor patterns. For example, the chip area may include a substrate, a gate pattern, a spacer pattern, an active pattern, and the like, and may include various types of film qualities. The substrate according to some embodiments of the present disclosure, for example, may be a relatively thick substrate, such as a silicon (Si) substrate, a glass substrate, and a sapphire substrate, and may be a substrate having a laminated structure such as an silicon-on-insulator (SOI) substrate.

An optical measurement apparatus 100 for measuring the semiconductor device according to an embodiment of the present disclosure may provide data on wavelength distribution characteristics of reflected light 106 reflected from the object to be measured 110, for example, spectrum data. The spectrum data may include information on intensity, reflectance and the like for each wavelength. In some embodiments of the present disclosure, the spectrum data may include multi-dimensional spectrum data, e.g., three-dimensional spectrum data.

Measurement of the object to be measured 110 may be performed by processing the spectrum data acquired from the optical measurement apparatus 100 with a candidate position selection unit 200, a candidate position analysis unit 210, and a prediction unit 220. The optical measurement apparatus 100 performs a first measurement of the object to be measured 110 and generates multi-dimensional spectrum data MS. In this embodiment, the first measurement may be performed on the entire area of the object to be measured 110, using a spectral imaging device.

The candidate position selection unit 200 receives the multi-dimensional spectrum data MS from the optical measurement apparatus 100, and selects the candidate position CP that is presumed to have a high possibility of detecting abnormality therefrom.

The candidate position analysis unit 210 performs a second measurement on the candidate position selected by the candidate position selection unit 200 to generate a candidate position measurement result CPR. In some embodiments of the present disclosure, the second measurement may include at least one of a transmission electron microscope (TEM) measurement, a scanning electron microscope (SEM) measurement, a reflection electron microscope (REM), and a scanning transmission electron microscope (STEM) measurement. That is, since the second measurement includes a point sampling type measurement unlike the first measurement, the second measurement may be performed to obtain a more precise analysis result on the candidate position CP.

Thereafter, the prediction unit 220 may predict the measurement result of other pixels, using the candidate position measurement result CPR calculated by the candidate position analysis unit 210. The specific description of the operations of the candidate position selection unit 200, the candidate position analysis unit 210 and the prediction unit 220 will be provided later in detail with reference to FIGS. 4 to 11.

The optical measurement apparatus 100 includes a light source 102 and a light detection unit 108. The light source 102 irradiates the measurement light having a predetermined wavelength range at a predetermined angle in order to measure the wavelength distribution characteristics of the reflected light 106 reflected from the object to be measured 110. The light detection unit 108 detects the electric signals of the respective wavelength components included in the reflected light 106 reflected from the object to be measured 110, and measures the spectrum of the wavelength domain that indicates the wavelength distribution characteristics (e.g., an amplitude ratio ($\psi$), a phase difference ($\Delta$), etc.).

As illustrated in FIG. 2, the optical measurement apparatus 100 according to some embodiments of the present disclosure further includes a polarizer 112 between the light source 102 and the object to be measured 110. Light generated by the light source 102 may be linearly polarized by the polarizer 112. Furthermore, the optical measurement apparatus 100 according to some embodiments of the present disclosure may further include an analyzer 118 between the object to be measured 110 and the light detection unit 108. The analyzer 118 may analyze the change in the polarization of the reflected light 106. Alternatively, according to some embodiments of the present disclosure, the optical measurement apparatus 100 may further include a compensator or a phase-modulator.

The optical measurement apparatus 100 according to an embodiment of the present disclosure may be a non-contact and non-destructive measurement apparatus capable of inspecting the object to be measured, without processing or deforming the object to be measured. In an embodiment of the present disclosure, the optical measurement apparatus 100 may be a spectral imaging device, a spectroscopic ellipsometer, or the like.

Figure 3:
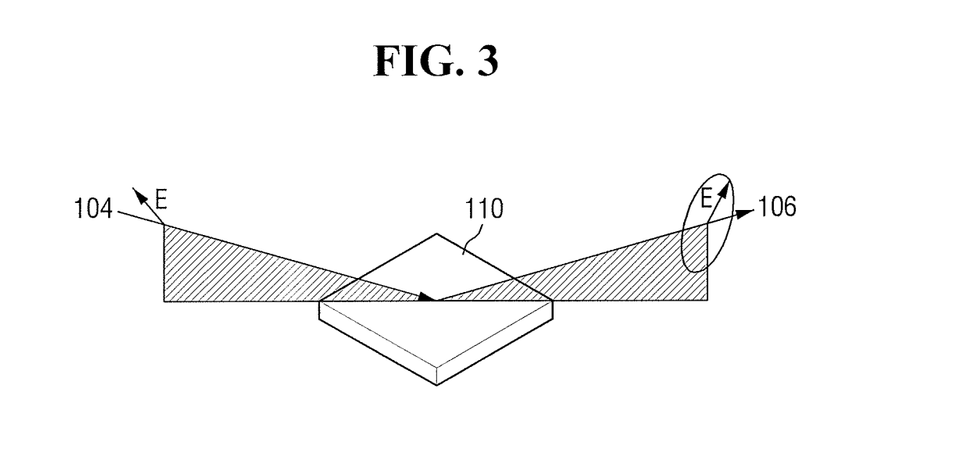
FIG. 3 illustrates a diagram for explaining the concept of measuring the thickness of an object to be measured, using the optical measurement apparatus of FIG. 1.

In FIG. 3, an example method for measuring the thickness of the object to be measured 110 using the optical measurement apparatus 100 will be described. However, this is only an example, and the optical measurement apparatus 100 according to various embodiments of the present disclosure may measure various dimensions of various semiconductor patterns formed on the object to be measured 110 in addition to or instead of the thickness.

FIG. 3 is a diagram for explaining the concept of measuring the thickness of the object to be measured, using the optical measurement apparatus of FIG. 1. Referring to FIGS. 1 and 33, in order to measure the thickness of the object to be measured 110, the light source 102 may irradiate the object to be measured 110 with the incident light 104. The optical measurement apparatus 100 may acquire a spectrum according to the wavelength of the reflected light 106 reflected from the surface of the measurement object 110, using the difference in refractive index according to the wavelength of light. Specifically, the optical measurement apparatus 100 may detect the spectrum corresponding to amplitude ratio ($\psi$) or the phase difference ($\Delta$) using birefringence in order to detect the microstructure, e.g., a contact hole, a trench and a line/space having a nano-size, on the surface of the object to be measured 110 with high resolution.

The polarization state of the incident light 104 may be decomposed into an s-polarization component and a p-polarization component. Here, the s-polarization component is a component that is perpendicular to the incident surface and vibrates to be parallel to the surface of the object to be measured 110, and the p-polarization component is a component that vibrates to be parallel to the incident surface. The s-polarization component and the p-polarization component of the reflected light 106 reflected from the surface of the object to be measured 110 have changes in the amplitude and phase, and the optical measurement apparatus 100 may measure such a change as a complex reflectance ratio ($\rho$). That is, the optical measurement apparatus 100 according to an embodiment of the present disclosure may measure the changed polarization state of the reflected light 106 which can be expressed by the following <Formula 1>.

$$\rho = \frac{r_p}{r_s} = \tan(\psi)e^{i\Delta} \qquad \langle \text{Formula 1} \rangle$$

Here, $r_p$ is the reflectance of the p-polarized component, $r_s$ is the reflectance of the s-polarized component, $\psi$ is the amplitude ratio ($\psi$) of the reflected light 106, and $\Delta$ is the phase difference of the reflected light.

The data of the amplitude ratio ($\psi$) or the phase difference ($\Delta$) of the reflected light 106 capable of being measured from the optical measurement apparatus 100 do not directly indicate the values of thickness of the object to be measured 110 or the optical constant. Further, the data of the amplitude ratio ($\psi$) or the phase difference ($\Delta$) of the reflected light 106 may not be directly converted into the values of thickness of the object to be measured 110 or the optical constant. Therefore, the data of the amplitude ratio ($\psi$) and/or the phase difference ($\Delta$) of the reflected light 106 measured from the optical measurement apparatus 100, i.e., the multi-dimensional spectrum data MS, is to be processed to determine the actual physical values, e.g., the thickness, of the object to be measured 110 or the optical constant.

Such a calculation process is generally performed by theoretical modelling measurement. Theoretical modelling measurement requires repeatedly adjusting the structural model parameters to make the theoretical spectrum obtained by the simulation coincide with the measured spectrum and a lot of time.

In order to solve such a problem, the method for measuring the semiconductor device according to various embodiments of the present disclosure measures a semiconductor device by a method different from a theoretical modelling measuring method, as described in detail below.

Figure 4:
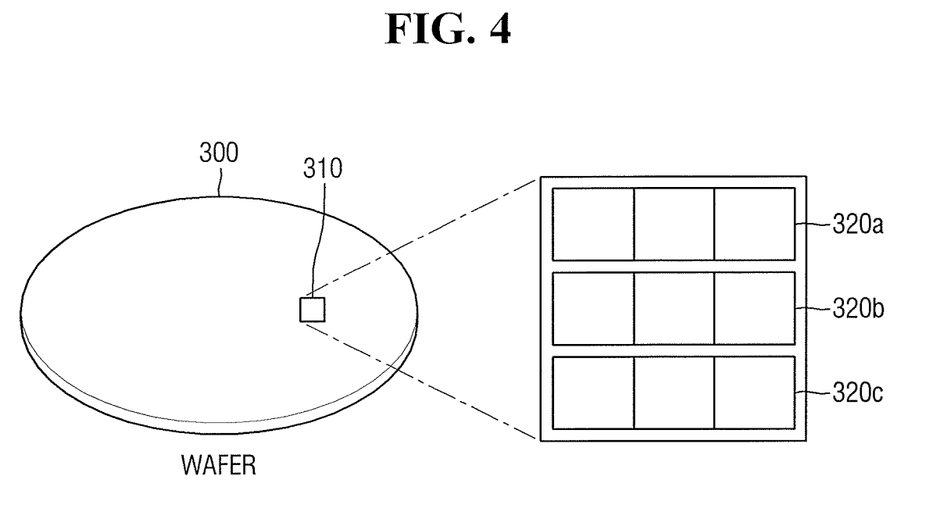
FIGS. 4 and 5 illustrate schematic diagrams for explaining a method for measuring a semiconductor device according to an embodiment of the present disclosure.
Figure 5:
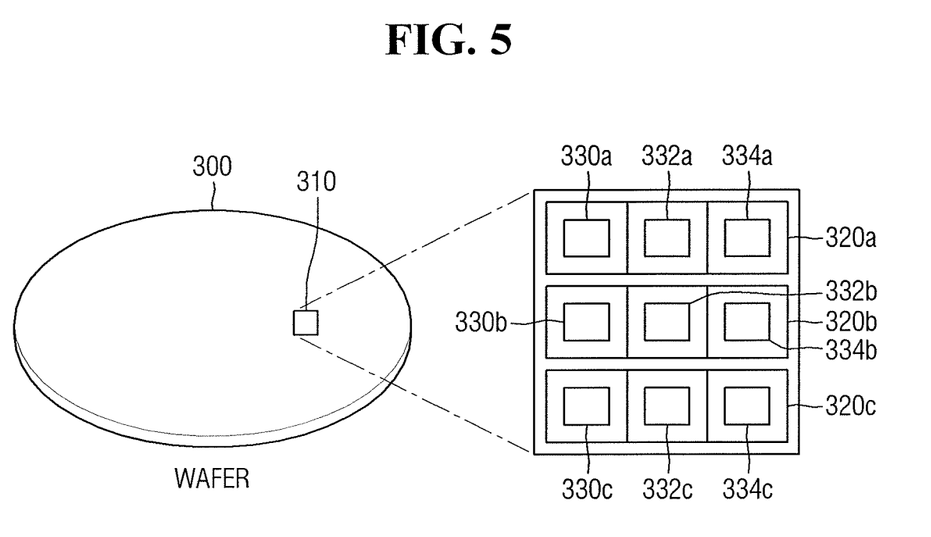

FIGS. 4 and 5 are schematic diagrams for explaining a method for measuring a semiconductor device according to an embodiment of the present disclosure.

Referring to FIG. 4, the wafer 300 may include one or more chip areas 310. In the present embodiment, the chip area 310 may include one chip die, but the scope of the present disclosure is not limited thereto. Various semiconductor pattern structures are formed in the chip area 310.

The candidate position selection unit 200 first defines interest areas 320a, 320b and 320c in the chip area 310 on the wafer 300. The interest areas 320a, 320b and 320c are areas which serve as analysis targets for abnormality detection among the chip areas. Specifically, the pixels on the image obtained by first measuring the interest areas 320a, 320b, and 320c with the spectral imaging device serve as the analysis targets.

Next, with reference to FIG. 5, the candidate position selection unit 200 includes acceptable areas 330a, 332a, 334a, 330b, 332b, 334b, 330c, 332c, and 334c in the chip area 310 on the wafer 300. The acceptable areas 330a, 332a, 334a, 330b, 332b, 334b, 330c, 332c, and 334c are referred to as areas in which standard spectrum data for abnormality detection can be acquired. For example, the spectrum data obtained by first measurement of the acceptable areas 330a, 332a, 334a, 330b, 332b, 334a, 330b, 332b, 334b, 330c, 332c, and 334c with the spectral imaging device are assumed to be the data of the acceptable range, and the spectrum data of arbitrary pixels located outside the acceptable areas 330a, 332a, 334a, 330b, 332b, 334b, 330c, 332c and 334c are compared on the basis thereof, thereby making it possible to detect abnormality.

In the present embodiment, the acceptable areas 330a, 332a, 334a, 330b, 332b, 334b, 330c, 332c and 334c are defined inside the interest areas 320a, 320b and 320c. However, this is merely an example, and the scope of the present disclosure is not limited thereto.

In order to detect abnormality, the candidate position selection unit 200 may assume the spectrum data of the first pixel in the acceptable areas 330a, 332a, 334a, 330b, 332b, 334b, 330c, 332c, and 334c, e.g., an acceptable distribution, has a normal distribution. Alternatively, the acceptable spectrum data of the first pixel may be assumed to have a multivariate normal distribution.

The candidate position selection unit 200 may calculate the distance from the central point on the acceptable distribution for the second pixels in the interest areas 320a, 320,b and 320c. In the present embodiment, the second pixel is in the interest areas 320a, 320b and 320c, but the second pixel may not be in the acceptable area 330a, 332a, 334a, 330b, 332b, 334b, 330c, 332c, and 334c.

After that, the candidate position selection unit 200 may select the position of the pixel, in which the distance from the central point exceeds a predetermined range on the acceptable distribution, among the second pixels, as the candidate position CP. The above configuration will be described again by way of an example. First, the acceptable areas 330a, 332a, and 334a may be defined inside the interest area 320a.

In this case, the semiconductor patterns distributed in the acceptable areas 330a, 332a and 334a are assumed to be formed in an acceptable range which generally does not deviate from the design range, and the distribution of the spectrum data of the first pixel in the acceptable areas 330a, 332a and 334a among the spectrum data acquired by first measurement of the chip area 310 with the spectral imaging device is assumed as the normal distribution. After that, the distance from the central point on the distribution of spectrum data of the first pixel is calculated on all the second pixels which are in the interest area 320a, but are not in the acceptable areas 330a, 332a and 334a.

Pixels in which the calculation result exceeds the predetermined range are selected as candidate positions at which a second measurement of a more precise point sampling type needs to be performed, as will be described later. In some embodiments of the present disclosure, for all second pixels which are in the interest area 320a, but are not in the acceptable areas 330a, 332a and 334a, the distance from the central point in the acceptable distribution of the spectrum data of the first pixel to the second pixel may be calculated as a Mahalanobis distance.

Hereinafter, referring to FIG. 6, a method for calculating the distribution of spectrum data of the first pixel with respect to the second pixel, that is, the distance to the central point to the distribution, using the Mahalanobis distance will be explained. It should be noted that the method for utilizing the Mahalanobis distance is merely an example for achieving the present disclosure, the scope of the present disclosure is not limited thereto, and it is obvious to those of ordinary skill in the art that it is possible to calculate distance from the central point in the acceptable distribution of the first pixel to the second pixel by various methods.

Figure 6:
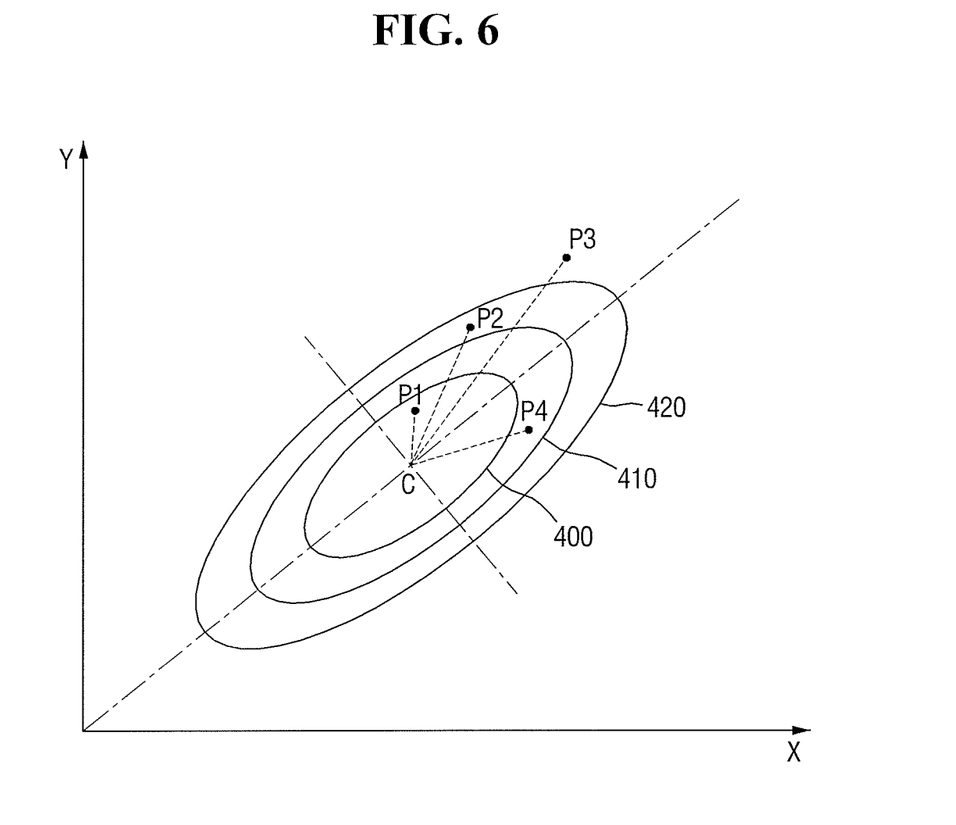
FIG. 6 illustrates a schematic diagram for explaining a method for measuring a semiconductor device according to another embodiment of the present disclosure.

FIG. 6 is a schematic diagram for explaining a method for measuring a semiconductor device according to another embodiment of the present disclosure. Referring to FIG. 6, as an example for explaining a method in which the candidate position selection unit 200 calculates the distance to the central point on the acceptable distribution for the second pixel, the positions on the acceptable distribution of all the pixels of the acceptable areas 330a, 332a, 334a, 330b, 332b, 334b, 330c, 332c, and 334c are illustrated as an image on the assumption that the spectrum data is two-dimensional.

The anomaly detection algorithm using the Mahalanobis distance is introduced as an RX-algorithm in [I. S. Reed and X. Yu, "Adaptive multiple-band CFAR detection of an optical pattern with unknown spectral distribution," IEEE Trans. Acoust., Speech Signal Process., Vol. 38, no. 10, pp. 1760-1770, October 1990], which has been widely used in the technical field.

The candidate position selection unit 200 calculates the Mahalanobis distance of the second pixel in the interest area from the distribution of spectrum data of the first pixel. This corresponds to the distance between the central point C of the acceptable distribution and the second pixel P1, P2, P3, and P4 in FIG. 6.

For example, considering a predetermined distance or range 400 as a reference, the pixel P1 in which the Mahalanobis distance does not exceed the predetermined range 400 is, for example, determined to be located inside the smallest ellipse in FIG. 6 and to fall within the acceptable range. In contrast, pixels P2 to P4 in which the Mahalanobis distance exceeds a predetermined range 400 are, for example, determined to have a high possibility of being located outside the smallest ellipse in FIG. 6 and falling within the abnormality range. Therefore, the positions of the pixels P2 to P4 are selected as the candidate positions CP, and the second measurement is performed on the candidate positions CP.

As another example, considering the predetermined distance or range 410 as a reference, the pixels P1 and P4 in which the Mahalanobis distance does not exceed the predetermined range 410 are, for example, determined to be located inside the second smallest ellipse and to fall within the acceptable range. Pixels P2 and P3 in which the Mahalanobis distance exceeds the predetermined range 410 are, for example, determined to have a high possibility of being located outside the second smallest ellipse in FIG. 6 and falling within the abnormality range. Therefore, the positions of the pixel P2 and P3 are selected as the candidate positions, and the second measurement is performed on the candidate positions.

As another example, considering a predetermined distance or range 420 as a reference, the pixels P1, P2, and P4 in which Mahalanobis distance does not exceed a predetermined range 420 are, for example, determined to be located inside the largest ellipse in FIG. 6 and to fall within the acceptable range. In contrast, the pixel P3 in which the Mahalanobis distance exceeds the predetermined range 420 is, for example, determined to have a high possibility of being located outside the largest ellipse in FIG. 6 and falling within the abnormality range. Therefore, the position of the pixel P3 is selected as the candidate position CP, and the second measurement is performed on the candidate position CP.

Setting of a boundary of the predetermined ranges 400, 410 and 420 may change depending on a specific measurement environment. In this way, after calculating the Mahalanobis distance on the second pixel, a Mahalanobis distance map in which the Mahalanobis distance of the second pixel is expressed by the numerical value may be generated, and the position of the pixel having an intensity that exceeds a predetermined value, among the second pixels, may be selected as a candidate position CP.

Specifically, the Mahalanobis distance map may include, for example, third pixels corresponding one-to-one to the pixels of the interest areas 320a, 320b, and 320c illustrated in FIG. 4 or 5, and each of the third pixels may express the numerical value of intensity. For example, the intensity of the third pixel may be determined to change in proportion to the Mahalanobis distance of the spectrum data. Accordingly, by selecting a third pixel having an intensity that exceeds a predetermined value, among the third pixels, the position of the second pixel corresponding to the selected third pixel among the second pixels may be selected as a candidate position.

Figures 7, 8:
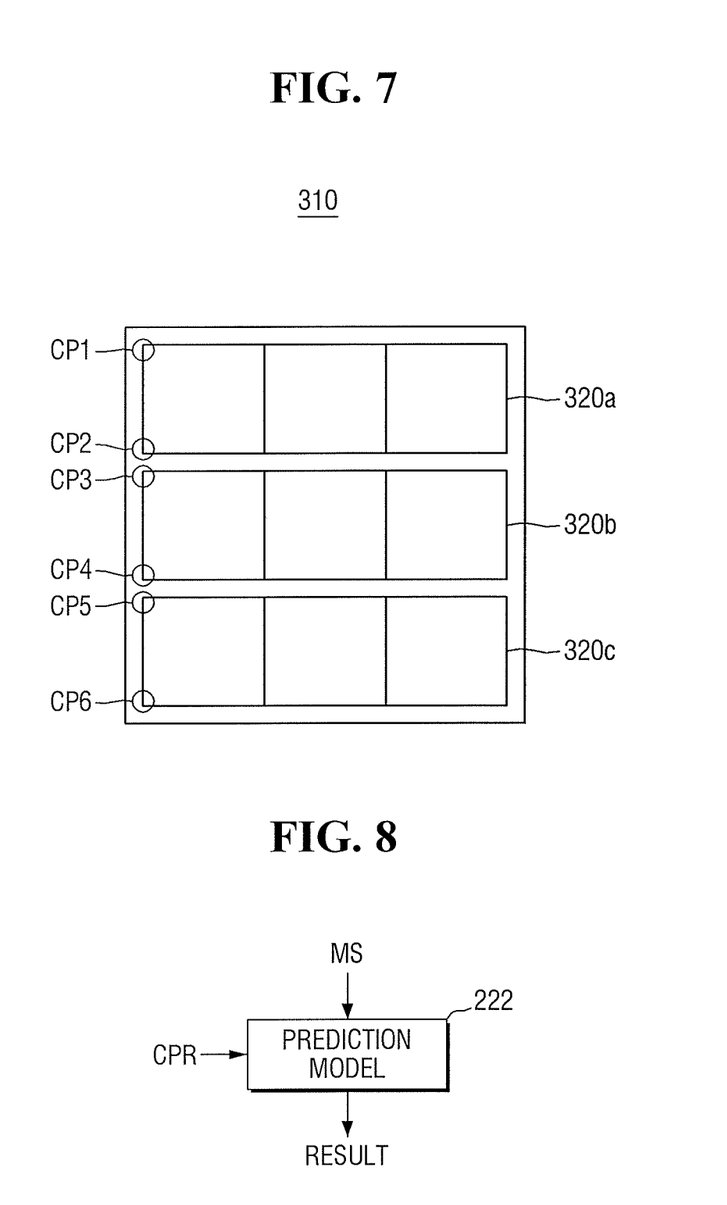
FIG. 7 illustrates a schematic diagram for explaining the method for measuring the semiconductor device according to the embodiment of FIGS. 4 to 6 of the present disclosure.
FIGS. 8 and 9 illustrate schematic diagrams for explaining a method for measuring a semiconductor device according to still another embodiment of the present disclosure.

FIG. 7 is a schematic diagram for explaining the method for measuring the semiconductor device according to the embodiment of FIGS. 4 to 6 of the present disclosure. Referring to FIG. 7, a candidate position CP may be selected by the method as described above.

That is, the candidate positions CP1 and CP2 are selected in the interest area 320a of the chip area 310, the candidate positions CP3 and CP4 are selected in the interest area 320b, and the candidate positions CP5 and CP6 are selected in the interest region 320c.

Now, the candidate position analysis unit 210 performs the second measurement of the point sampling type on the candidate positions CP1 to CP6. In some embodiments of the present disclosure, the second measurement may include at least one of a transmission electron microscope (TEM) measurement, a scanning electron microscope (SEM) measurement, a reflection electron microscope (REM) and a scanning transmission electron microscope (STEM) measurement.

According to the embodiments of the present disclosure explained so far, the spectrum analysis is primarily performed over the entire areas of the wafer 300 (or the chip area 310) using a spectral imaging device, the candidate position requiring for the precise analysis is selected, and thereafter, the analysis of more precise point sampling type is secondarily performed on the candidate position, thereby enabling the measurement with shortened analysis time.

Figure 9:
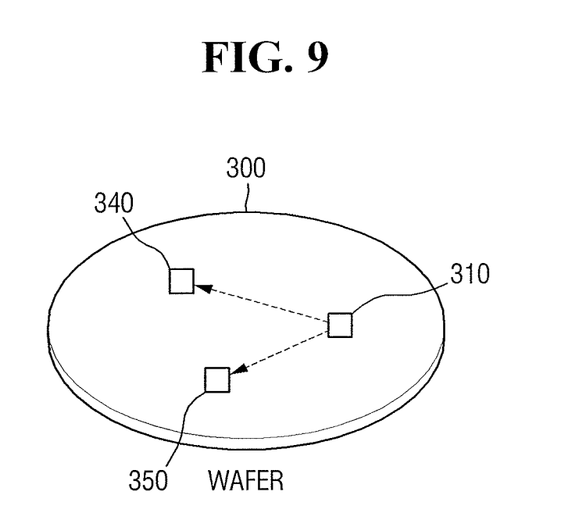

FIGS. 8 and 9 are schematic diagrams for explaining a method for measuring a semiconductor device according to another embodiment of the present disclosure.

Referring to FIG. 8, when the candidate position analysis unit 210 performs the second measurement of the point sampling type on the candidate positions CP1 to CP6 to calculate the candidate position measurement result CPR (i.e., result for the second measurement), the prediction unit 220 may predict the measurement results of other pixels than the interest areas 320a, 320b, and 320c, using the candidate position measurement result CPR of the candidate positions CP1 to CP6.

Specifically, the prediction unit 220 may learn a prediction model based on a supervised learning algorithm, using the candidate position measurement result CPR. Further, the prediction unit 220 may predict the measurement result of other pixels than the interest areas 320a, 320b, and 320c, using the learned prediction model. In some embodiments of the present disclosure, the supervised learning algorithm may include regression analysis algorithms or classification algorithms, but the scope of the present disclosure is not limited thereto.

Referring to FIG. 9, the prediction unit 220 may apply the measurement results to other chip areas 340 and 350 of the wafer 300. Specifically, the prediction unit 220 may also predict the measurement results of the pixels in the second chip areas 340 and 350, using the second measurement result performed on the first chip area 310.

According to the embodiment of the present disclosure explained so far, the spectrum analysis is primarily performed over the entire areas of the wafer 300 (or the chip area 310) using a spectral imaging device, the candidate position requiring for the precise analysis is selected, and thereafter, as a result obtained after secondarily performing the analysis of more precise point sampling type on the candidate position, the measurement result of other chip areas and the entire areas of the wafer is predicted, thereby enabling the measurement with reduced analysis time, while enabling the measurement of the entire areas of the wafer.

On the other hand, for example, when the second measurement is a TEM measurement, a TEM supervision may be generated over the entire area of the wafer or the entire area of the chip area which is difficult to be achieved by physical measurement through such a prediction method.

Figure 10:
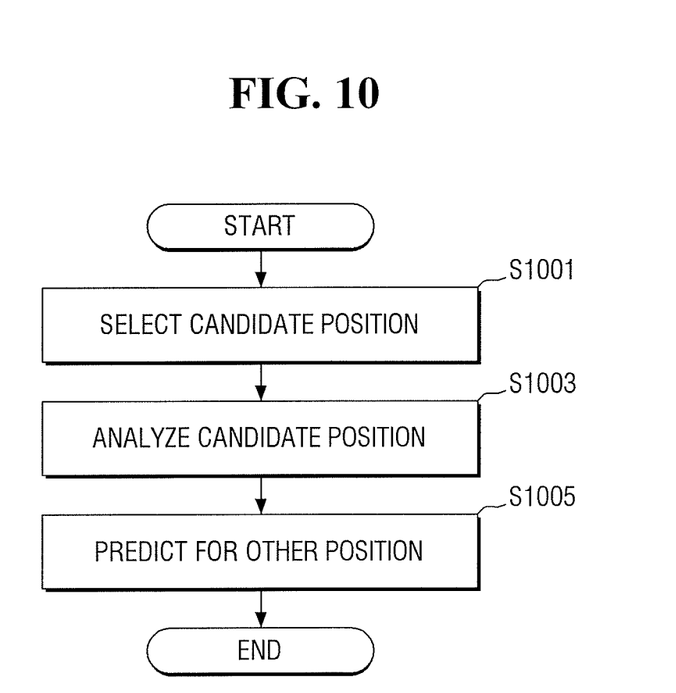
FIGS. 10 and 11 illustrate flowcharts for explaining the method for measuring the semiconductor device according to an embodiment of the present disclosure.
Figure 11:
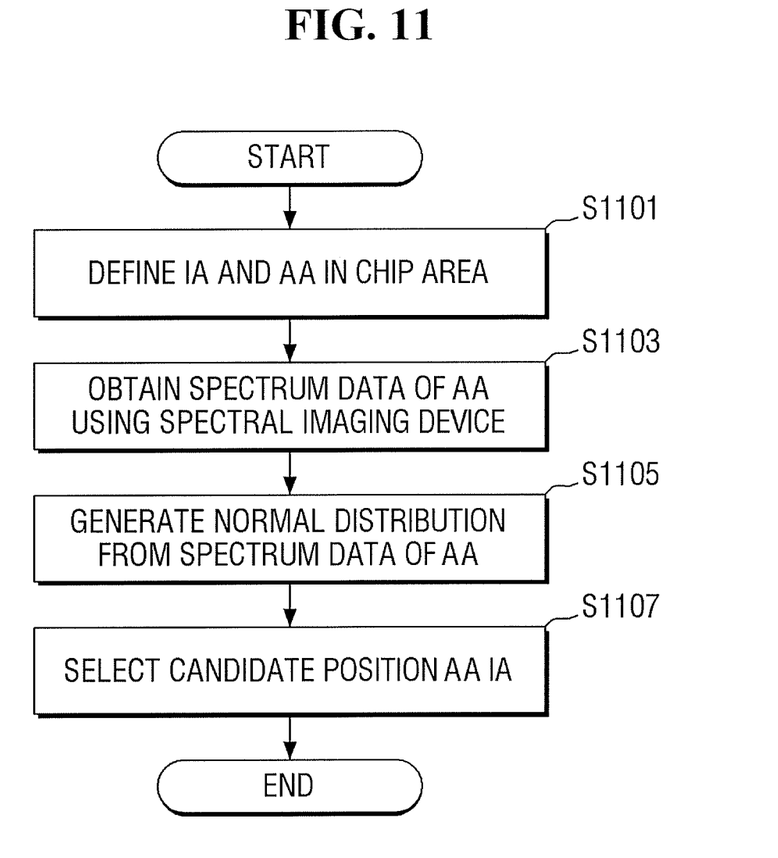

FIGS. 10 and 11 are flowcharts for explaining a method for measuring a semiconductor device according to an embodiment of the present disclosure. Referring to FIG. 10, in the above method, the candidate positions are first selected (S1001). Specifically, referring to FIG. 11 together with FIG. 10, an interest area IA and an acceptable area AA are defined in the chip area on the wafer (S1101).

Next, the chip area, in particular, the acceptable areas AA is first measured with the spectral imaging device to obtain the spectrum data thereof (S1103). Among them, an acceptable distribution is generated from the spectrum data of the first pixel in the acceptable area AA, which is assumed to be a normal distribution (S1105). In some embodiments of the present disclosure, the generation of the normal distribution may include a generation of a Mahalanobis distance map described in connection with FIG. 6.

Distances from the central point in the normal distribution to second pixels in the interest area IA are calculated. A position of a second pixel, among the second pixels, having a distance from the central point of the normal distribution that exceeds the predetermined range is selected as the candidate position (S1107).

Referring to FIG. 10 again, the second measurement for performing the precise analysis on the candidate position is performed (S1003). As described above, the second measurement may be a measurement of point sampling type.

Thereafter, the measurement result may also be predicted for other pixels than the interest area IA, using the second measurement result of the candidate position (S1005).

According to various embodiments of the present disclosure described above, it is possible to provide a measurement method capable of predicting the measurement of the entire areas of the wafer, while allowing the measurement with reduced analysis time.

Figure 12:
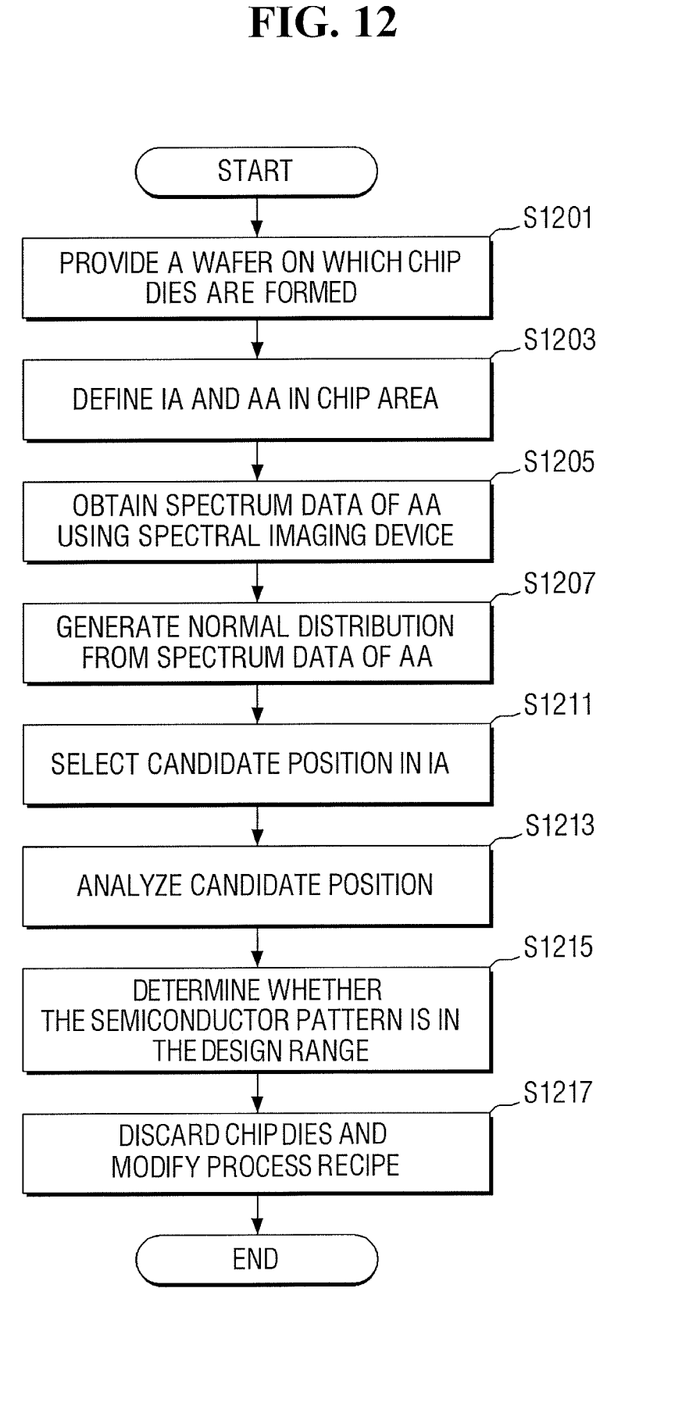
FIG. 12 is a flowchart for explaining a method for fabricating a semiconductor device according to an embodiment for the present disclosure.

FIG. 12 is a flowchart for explaining a method for fabricating a semiconductor device according to an embodiment for the present disclosure.

Referring to FIG. 12, in the above method, a wafer on which chip dies are formed is provided (S1201), and an interest area IA and an acceptable area AA are defined in a chip area on the wafer (S1203).

Next, the chip area, in particular, the acceptable areas AA is first measured with the spectral imaging device to obtain the spectrum data thereof (S1205). Among them, an acceptable distribution is generated from the spectrum data of the first pixel in the acceptable area is generated from the spectrum data of the first pixel in the acceptable area AA, which is assumed to be a normal distribution (S1207). In some embodiments of the present disclosure, the generation of the normal distribution may include a generation of a Mahalanobis distance map described in connection with FIG. 6.

Next, distances from the central point in the normal distribution to second pixels in the interest area IA are calculated. A position of a second pixel, among the second pixels, having a distance from the central point of the normal distribution that exceeds the predetermined range is selected as the candidate position (S1209).

The second measurement for performing the precise analysis on the candidate position is performed (S1211). In some measurement of the present disclosure, learning a prediction model based on a supervised learning algorithm using the second measurement, and predicting a measurement of pixels other than the interest area using the learned prediction model may be further performed.

Next, it is determined whether structures of the semiconductor patterns formed on the chip die on the wafer by the result of the second measurement e.g. the thicknesses of the semiconductor patterns are included within the design range (S1213). If the result of the second measurement for the interest area IA is not included within the design range, the manufactured chip die is discarded and a process recipe for the interest region AA may be modified (S1215).

The methods and processes described herein may be performed by code or instructions to be executed by a computer, processor, manager, or controller. Because the algorithms that form the basis of the methods (or operations of the computer, processor, or controller) are described in detail, the code or instructions for implementing the operations of the method embodiments may transform the computer, processor, or controller into a special-purpose processor for performing the methods described herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method embodiments described herein.

Embodiments are described, and illustrated in the drawings, in terms of functional blocks, units and/or modules. Those skilled in the art will appreciate that these blocks, units and/or modules are physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units and/or modules being implemented by microprocessors or similar, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the embodiments may be physically separated into two or more interacting and discrete blocks, units and/or modules without departing from the scope of the disclosure. Further, the blocks, units and/or modules of the embodiments may be physically combined into more complex blocks, units and/or modules without departing from the scope of the disclosure.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A method for measuring a semiconductor device, the method comprising:
    defining an interest area and an acceptable area in a chip area on a wafer;
    performing a first measurement of the chip area with a spectral imaging device to acquire spectrum data of the chip area;
    assuming a distribution of spectrum data of a first pixel in the acceptable area is a normal distribution;
    calculating a distance from a central point on the normal distribution to second pixels in the interest area;
    selecting a position of a second pixel having a distance from the central point on the normal distribution greater than a predetermined range, among the second pixels, as a candidate position;
    performing a second measurement of the candidate position; and
    predicting a measurement of pixels other than the interest area, using the second measurement of the candidate position, predicting the measurement including:
        learning a prediction model based on a supervised learning algorithm, using the second measurement; and
        predicting a measurement of pixels other than the interest area, using the learned prediction model.

2. The method as claimed in claim 1, wherein assuming the distribution of spectrum data of the first pixel is a normal distribution includes:
    assuming the distribution of spectrum data of the first pixel is a multivariate normal distribution.

3. The method as claimed in claim 1, wherein calculating a distance from the central point on the normal distribution to the second pixel includes:
    calculating a Mahalanobis distance to the second pixel from a central pixel of the distribution of spectrum data of the first pixel; and
    calculating a distance from the central point on the normal distribution for the second pixel, using the Mahalanobis distance.

4. The method as claimed in claim 3, further comprising:
    generating a Mahalanobis distance map in which the Mahalanobis distance of the second pixel is expressed by a numerical value of intensity,
    wherein selecting a position of a pixel as the candidate position includes:
    selecting a position of a pixel having an intensity that exceeds a predetermined value, among second pixels, as the candidate position.

5. The method as claimed in claim 1, wherein the acceptable area is defined inside the interest area.

6. The method as claimed in claim 1, wherein the second pixel is in the interest area but is not in the acceptable area.

7. The method as claimed in claim 1, wherein the supervised learning algorithm includes a regression analysis algorithm or a classification algorithm.

8. A method for measuring a semiconductor device, the method comprising:
    defining an interest area and an acceptable area in a chip area on a wafer;
    performing a first measurement of the chip area with a spectral imaging device to acquire spectrum data of the chip area;
    calculating a Mahalanobis distance on a second pixel in the interest area from a distribution of spectrum data of a first pixel in the acceptable area;
    generating a Mahalanobis distance map in which the Mahalanobis distance of the second pixel indicates an intensity value;
    selecting a position of a pixel having an intensity value that exceeds a predetermined value as a candidate position; and
    performing a second measurement of the candidate position.

9. The method as claimed in claim 8, wherein the acceptable area is defined inside the interest area.

10. The method as claimed in claim 9, wherein the second pixel is in the interest area but is not in the acceptable area.

11. The method as claimed in claim 8, wherein the spectrum data includes multi-dimensional spectrum data.

12. The method as claimed in claim 8, further comprising:
    predicting a measurement of pixels other than the interest area, using the second measurement of the candidate position.

13. The method as claimed in claim 12, wherein the chip area includes a first chip area and a second chip area, and wherein predicting the measurement includes:
    predicting a measurement of pixels in the second chip area using the second measurement performed on the first chip area.

14. The method as claimed in claim 12, wherein predicting a measurement includes:
    learning a prediction model based on a supervised learning algorithm, using the second measurement; and
    predicting a measurement of pixels other than the interest area, using the learned prediction model.

15. The method as claimed in claim 14, wherein the supervised learning algorithm includes a regression analysis algorithm or a classification algorithm.

16. A method for measuring a semiconductor device, the method comprising:
    defining an interest area and an acceptable area in a chip area on a wafer;
    performing a first measurement of the chip area with a spectral imaging device to acquire spectrum data of the chip area;
    assuming a distribution of spectrum data of a first pixel in the acceptable area is a normal distribution;
    calculating a distance from a central point on the normal distribution to second pixels in the interest area, wherein calculating a distance from the central point on the normal distribution to the second pixel includes:
        calculating a Mahalanobis distance to the second pixel from a central pixel of the distribution of spectrum data of the first pixel; and
        calculating a distance from the central point on the normal distribution for the second pixel, using the Mahalanobis distance;
    selecting a position of a second pixel having a distance from the central point on the normal distribution greater than a predetermined range, among the second pixels, as a candidate position; and
    performing a second measurement of the candidate position.

* * * * *